United States Patent [19]

Matsunaga et al.

[11] 4,288,637

[45] Sep. 8, 1981

[54] PROCESS FOR PREPARATION OF AROMATIC HYDROPEROXIDES

[75] Inventors: Fujihisa Matsunaga, Iwakuni; Yoshiyuki Shinohara, Kashiwa; Isamu Okubo, Ohtake; Takayuki Nakamura, Iwakuni; Seiichi Tanaka, Ohtake, all of Japan

[73] Assignee: Mitsui Petrochemical Industries, Ltd., Tokyo, Japan

[21] Appl. No.: 143,474

[22] Filed: Apr. 24, 1980

[30] Foreign Application Priority Data

Apr. 27, 1979 [JP] Japan .................................. 54-51537

[51] Int. Cl.$^3$ .......................................... C07C 179/035
[52] U.S. Cl. .................................... 568/575; 568/574
[58] Field of Search ................................ 568/574, 575

[56] References Cited

U.S. PATENT DOCUMENTS

| | | | |
|---|---|---|---|
| 2,595,266 | 5/1952 | Johnson | 568/575 |
| 2,664,448 | 12/1953 | Lorand et al. | 568/575 |
| 3,666,815 | 5/1972 | Scheltus | 568/575 |
| 3,845,140 | 10/1974 | Brownstein et al. | 568/575 |
| 4,013,725 | 3/1977 | Yonemitsu et al. | 568/575 |

FOREIGN PATENT DOCUMENTS 745128  2/1956  United Kingdom .

Primary Examiner—Werren B. Lone

[57] ABSTRACT

Disclosed is a process for the preparation of aromatic hydroperoxides comprising contacting two liquid phases comprising an oily phase containing an aromatic compound having a secondary alkyl group and a basic aqueous phase under agitation with a molecular oxygen-containing gas in the presence of a copper compound catalyst such as an inorganic salt or organic acid salt of copper, thereby to oxidize the aromatic compound to a corresponding aromatic hydroperoxide, wherein the liquid phase catalytic oxidation is carried out while maintaining the catalyst concentration in the liquid phases at 0.005 to 10 ppm as the copper atom and the pH value of the basic aqueous phase at 7.6 to 10. According to this process, by adoption of the above-mentioned specific catalyst concentration and pH value in combination, the rate of oxidation of the aromatic compound is increased and the selectivity to the hydroperoxide is improved.

8 Claims, No Drawings

PROCESS FOR PREPARATION OF AROMATIC HYDROPEROXIDES

BACKGROUND OF THE INVENTION (1) Field of the Invention

The present invention relates to a process for the preparation of aromatic hydroperoxides in which an aromatic compound having a secondary alkyl group is subjected to liquid phase catalytic oxidation with a molecular oxygen-containing gas in the presence of a copper compound catalyst and a basic aqueous solution, whereby the rate of oxidation of the aromatic compound is increased and a corresponding aromatic hydroperoxide is prepared in a high yield.

(2) Description of the Prior Art

A process for preparing aromatic hydroperoxides by subjecting an aromatic compound having a secondary alkyl group, such as cumene, cymene, dimethylcumene, diisopropylbenzene or sec-butylbenzene, to liquid phase oxidation with a molecular oxygen-containing gas in the presence of a basic aqueous solution is well known, and this process is industrially carried out for the preparation of precursors of phenols. Also a process for preparing aromatic hydroperoxides by subjecting an aromatic compound having a secondary alkyl group, such as mentioned above, to liquid phase oxidation with a molecular oxygen-containing gas in the absence of a basic aqueous solution is known. Since the rate of this liquid phase oxidation is low in these known processes, there have been proposed processes for increasing the oxidation rate in which the liquid phase oxidation reaction is carried out in the presence of a catalyst of a compound of a heavy metal such as copper, manganese, cobalt, nickel or iron (see the specifications of British Pat. No. 665,897, British Pat. No. 665,898, British Pat. No. 745,128, British Pat. No. 760,367, British Pat. No. 801,387 and U.S. Pat. No. 2,954,405, Japanese Patent Publications No. 36899/70, No. 38604/70, No. 6568/71 and No. 7148/74, and Japanese Patent Application Laid-Open Specifications No. 507/73 and No. 72225/74). However, in each of these processes, the rate of the liquid phase catalytic oxidation is not sufficiently high. Especially when the aromatic compound to be oxidized is an aromatic compound having a primary alkyl group as well as a secondary alkyl group, such as cymene, dimethylcumene or diisopropyltoluene, the oxidation rate is much lower than in case of an aromatic compound having a secondary alkyl group alone, and furthermore, a primary aromatic hydroperoxide or secondary aromatic hydroperoxide is competitively formed as the oxidation product in addition to an intended tertiary aromatic hyroperoxide, resulting in reduction of the selectivity of the oxidation reaction. As means for improving the selectivity in the liquid phase catalytic oxidation of an aromatic compound having a secondary alkyl group and a primary alkyl group, there has been proposed a process in which the liquid phase catalytic oxidation is carried out in the presence of a heavy metal compound catalyst and an aqueous phase by using a molecular oxygen-containing gas (see Japanese Patent Application Laid-Open Specifications No. 142526/75 and No. 142527/75). According to these proposals, especially the proposal of Japanese Patent Application Laid-Open Specification No. 142,527/75, a chelate compound of a heavy metal is used as the catalyst and the liquid phase catalytic reaction is carried out while adjusting the pH value of the aqueous phase in the weakly acidic or neutral region, that is, to 5 to 7.5. According to this process, the selectivity to the tertiary aromatic hydroperoxide is improved to some extent, but decomposition of the aromatic hydroperoxide is advanced considerably in the catalytic oxidation system and phenol compounds are formed as by-products. Since these phenol compounds rather inhibit the oxidation reaction, there is brought about a problem of reduction of the oxidation rate.

SUMMARY OF THE INVENTION

We made researches with a view to increasing the oxidation rate and preparing an aromatic hydroperoxide selectively in a high yield in the process for preparing aromatic hydroperoxides by subjecting an aromatic compound having a secondary alkyl group to liquid phase catalytic oxidation with a molecular oxygen-containing gas in the presence of a copper compound catalyst and a basic aqueous solution. As the result, it was found that when an inorganic salt or organic acid salt of copper is used as the copper compound catalyst and the liquid phase catalytic oxidation is carried out while maintaining the copper compound concentration of the pH value of the basic aqueous phase at specific levels, the foregoing objects can be attained. We have now completed the present invention based on this finding. According to the process of the present invention, there can be attained not only an effect of improving the oxidation rate over the oxidation rates attainable by the conventional processes using an oxidation catalyst, but also an effect of preparing a tertiary aromatic hydroperoxide selectively in a high yield at an increased oxidation rate even if an aromatic compound having a primary alkyl group as well as a secondary alkyl group is used as the compound to be oxidized.

More specifically, in accordance with the present invention, there is provided a process for the preparation of aromatic hydroperoxides comprising contacting two liquid phases comprising an oily phase containing an aromatic compound having a secondary alkyl group and a basic aqueous phase under agitation with a molecular oxygen-containing gas in the presence of a copper compund catalyst, thereby to oxidize the aromatic compound to a corresponding aromatic hydroperoxide, wherein an inorganic salt or organic acid salt of copper is used as the copper compound catalyst and the liquid phase catalytic oxidation is carried out while maintaining the concentration of the copper compound catalyst in the liquid phases at 0.005 to 10 ppm as the copper atom and the pH value of the basic aqueous phase at 7.6 to 10.

DETAILED DESCRIPTION OF THE PREFERRED EMBODIMENTS

In the present invention, an aromatic compound having a secondary alkyl group is used as the compound to be oxidized. This aromatic compound may have a substituent not inhibiting the liquid phase catalytic oxidation reaction in addition to the secondary alkyl group. More specifically, there can be mentioned, for example, cumene, cymenes such as o-cymene, p-cymene and a mixture of cymene isomers, dimethylcumenes such 3,5-dimethylcumene, 3,4-dimethylcumene and 2,6-dimethylcumene, ethylcumene, sec-butylbenzene, diisopropylbenzenes such as o-diisopropylbenzene, m-diisopropylbenzene, p-diisopropylbenzene and a mixture of diisopropylbenzene isomers, and 3,5-diisopropyltoluene. Among these aromatic compounds having a secondary alkyl group, there are preferably used aromatic compounds having a secondary alkyl group and a primary alkyl group, which are represented by the following formula:

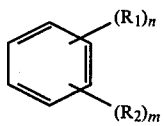

wherein $R_1$ stands for a secondary alkyl group having 3 to 4 carbon atoms, $R_2$ stands for a primary alkyl group having up to 4 carbon atoms, and n and m are numbers of 1 or 2 with the proviso that the sum of n and m does not exceed 3.

Aromatic compounds having a secondary alkyl group and a methyl group are especially preferred. Cymene, dimethylcumene or diisopropyltoluene is particularly especially preferred because the oxidation rate is remarkably improved and a corresponding tertiary aromatic hydroperoxide is prepared selectively in a high yield.

In the process of the present invention, the liquid phase catalytic oxidation of an aromatic compound having a secondary alkyl group is carried out in the presence of a basic aqueous solution. As the base contained in this basic aqueous solution, there can be mentioned, for example, alkali metal-containing bases such as lithium hydroxide, sodium hydroxide, potassium hydroxide, lithium carbonate, sodium carbonate, potassium carbonate, sodium bicarbonate, potassium bicarbonate, sodium acetate, potassium acetate, sodium propionate, potassium propionate, sodium benzoate, sodium toluylate and sodium cuminate, and alkaline earth metal-containing bases such as magnesium hydroxide and barium hydroxide. Such base is used in the form of an aqueous solution. In the present invention, it is indispensable that the pH value of the basic aqueous solution should be maintained at 7.6 to 10 during the catalytic oxidation reaction. In order to increase the oxidation rate and improve the selectivity, it is preferred that the pH value of the basic aqueous solution be maintained at 7.7 to 8.7. If the pH value of the basic aqueous solution is lower than 7.6 or higher than 10 at the catalytic oxidation reaction, the oxidation rate is remarkably reduced and the selectivity to the tertiary aromatic hydroperoxide is drastically lowered. Moreover, if the pH value of the basic aqueous solution is higher than 10, the copper compound catalyst is precipitated and the catalytic activity is drastically lowered. The volume ratio of the basic aqueous solution to the oily phase containing the aromatic compound having a secondary alkyl group is ordinarily 0.01 to 1, and when this volume ratio is in the range of from 0.02 to 0.5, the oxidation rate is particularly increased and the selectivity to the tertiary aromatic hydroperoxide is further improved.

In the process of the present invention, it is indispensable that an inorganic salt or organic acid salt of copper should be used as the copper compound catalyst while maintaining the pH value of the basic aqueous phase within the above-mentioned range. When the above-mentioned copper chelate compound disclosed in Japanese Patent Application Laid-Open Specification No. 142527/75 is used as the copper compound catalyst, the catalyst is inactivated in the above-mentioned pH range and the intended objects of the present invention cannot be attained at all. By selecting and using an inorganic salt or organic acid salt of copper, the activity of the catalyst can be maintained at a high level even when the pH value of the basic aqueous phase is within the above-mentioned range, and the oxidation rate can be increased and the selectivity to the aromatic hydroperoxide can be improved.

As the inorganic salt of copper that is used as the copper compound catalyst in the process of the present invention, there can be mentioned, for example, copper (I) chloride, copper (II) chloride, copper (I) fluoride, copper (II) fluoride, copper (I) bromide, copper (II) bromide, copper (I) iodide, copper (II) iodide, copper (II) sulfate, copper (II) nitrate, copper (II) nitride, copper (II) perchlorate, copper (I) carbonate, copper (I) oxide, copper (II) oxide, copper (II) phosphate, copper (II) pyrophosphate, copper (II) potassium sulfate, copper (II) sulfide, copper (I) cyanide, copper (II) cyanide, copper thiocyanate, sodium copper (II) cyanide, potassium copper cyanide, copper (II) tungstate, copper (II) borate, copper (II) arsenite, copper (II) borofluoride, copper (II) chromate, copper (II) hydroxide, copper (II) selenate and copper (II) silicofluoride. As the organic acid salt of copper, there can be mentioned, for example, copper (II) formate, copper (II) acetate, copper (II) propionate, copper (II) butyrate, copper (II) oxalate, copper (II) tartrate, copper (II) citrate, copper (II) laurate, copper (II) oleate, copper (II) salycilate, copper (II) stearate and copper (II) sulfamate. It is preferred that at least one compound selected from the group consisting of copper (II) nitrate, copper (II) perchlorate, copper (II) sulfate, copper (II) phosphate, copper (II) acetate, copper (II) benzoate and copper (II) citrate be used as the copper compound catalyst.

In the process of the present invention, the liquid phase catalytic oxidation reaction is carried out in the presence of a copper compound catalyst as mentioned above. The copper compound catalyst should be used in such an amount that the copper compound catalyst concentration in the liquid phases, that is, the oily phase containing the starting aromatic compound having a secondary alkyl group and the formed aromatic hydroperoxide and the basic aqueous phase, is 0.05 to 10 ppm, preferably 0.002 to 5 ppm, especially preferably 0.05 to 3 ppm, as the copper atom. If the amount used of the copper compound catalyst is larger than 10 ppm as the copper atom, decomposition of the aromatic hydroperoxide by the catalytic action of the copper catalyst becomes considerable and cannot be neglected, and the selectivity to the intended aromatic hydroperoxide is reduced. If the copper concentration is lower than 0.005 ppm, no substantial improvement of the oxidation rate or selectivity is attained As the molecular oxygen-containing gas that is used in the present invention, there can be mentioned air and a gaseous mixture of oxygen and an inert gas having an optional oxygen concentration. Air is especially preferred.

In the process of the present invention, the liquid phase catalytic oxidation of the aromatic compound having a secondary alkyl group is performed by contacting two liquid phases comprising the oily phase containing the aromatic compound having a secondary alkyl group and the basic aqueous phase under agitation with a molecular oxygen-containing gas. Ordinarily, the aromatic compound having a secondary alkyl group is used in a large excess, and the liquid phase catalytic oxidation is carried out in the absence of a particular reaction solvent. A solvent capable of dissolving therein the aromatic compound having a secondary alkyl group, which is insoluble in the basic aqueous solution phase and inactive to the oxidation, may be used as the reaction solvent. For example, there may be used inert solvents such as benzene, chlorobenzene, dichlorobenzene and trifluoromethylbenzene. When the solvent is used, the weight ratio of the solvent to the aromatic compound having a secondary alkyl group is ordinarily in the range of from 0.01 to 100. During the liquid phase oxidation or after the liquid phase oxidation, the oily phase contains the starting aromatic compound having a secondary alkyl group, the formed aromatic hydroperoxide, oil-soluble by-products and a minute amount of the copper compound catalyst, and the solvent incorporated according to need. The basic aqueous phase contains the basic substance as mentioned above, water-soluble by-products, the organic acid salt formed as the by-product and the majority of the copper compound catalyst.

In the process of the present invention, the liquid phase catalytic oxidation reaction is ordinarily carried out under heating, and the reaction temperature is ordinarily in the range of from room temperature and 200° C., preferably 60° to 150° C. The reaction pressure is 1 to 50 $Kg/cm^2$-G. The reaction is carried out under agitation. Especially good results are obtained when the oily phase containing the aromatic compound having a secondary alkyl group and the basic aqueous solution phase are mixed under agitation, preferably so that a water-in-oil suspension or emulsion is formed and the two liquid phases are sufficiently contacted with a molecular oxygen-containing gas. For this purpose, there may used a perforated plate or agitator, and when a draft tube or the like is disposed in an oxidation reaction vessel, the state of contact of the two liquid phases with the molecular oxygen-containing gas can be improved. The liquid phase catalytic oxidation reaction can be carried out in the presence of a radical initiator, and any of the continuous process, the semi-continuous process and the batchwise process may be adopted. If the reaction mixture is allowed to stand still after the reaction, the mixture is separated into the two liquid phases, the oily phase and the basic aqueous phase. The basic aqueous phase may be recycled to the reaction system and used again. If the solvent is contained in the oily phase, the solvent is removed by distillation, and the residual mixture is supplied to the step of acid decomposition of the obtained aromatic hydroperoxide directly or after distillation of the unreacted starting compound, whereby the corresponding phenol can be obtained.

The present invention will now be described in detail by reference to the following Examples that by no means limit the scope of the invention.

EXAMPLES 1 TO 6

A stainless steel continuous oxidation reaction vessel having a capacity of 7 liters and being equipped with a reflux cooler disposed in the upper portion to condense the vapor carried away by excessive air, an air introducing pipe in the lower portion, a pipe for introducing the starting material, catalyst and basic aqueous solution, a pipe for withdrawal of the liquid reaction mixture and an agitator was charged with a mixture of m- and p-cymenes, an aqueous solution of copper (II) sulfate and a 4% aqueous solution of sodium carbonate, which were supplied at predetermined flow rates. Continuous oxidation was carried out while blowing air at a predetermined rate into the reaction vessel until the concentration of cymene hydroperoxide (hereinafter referred to as "CyHP") in the liquid reaction mixture arrived at a stationary level. The oxidation product was subjected to oil-water separation. CyHP was analyzed according to the customary iodometry method, and unreacted cymene and oxidation by-products were analyzed according to gas chromatography.

Conditions adopted for the above oxidation process were a reaction temperature of 120° C., a reaction pressure of 5 $Kg/cm^2$-G, an agitation rate of 750 rpm, an oil phase/aqueous phase volume ratio of 9/1 and a copper atom concentration of 0.07, 0.18, 0.44, 0.63, 1.03 or 2.89 ppm based on the liquid phase (oily phase+aqueous phase). In this continuous oxidation of cymene, the CyHP concentration in the oxidation product oil was adjusted to 14 to 15 % by weight by controlling the feed rate of cymene. The pH of the aqueous phase was adjusted to 7.8 to 8.1 by controlling the feed rate of the aqueous solution of sodium carbonate. The agitation condition in the reaction vessel was set so that a water-in-oil emulsion was formed. The obtained results are shown in Table 1.

TABLE 1

| Example No. | Copper Atom Concentration (ppm) | CyHP Accumulation Rate (g/l . hr) *1 | Oxidation Efficiency (mol %) *2 |
| --- | --- | --- | --- |
| 1 | 0.07 | 48 | 79 |
| 2 | 0.18 | 53 | 80 |
| 3 | 0.44 | 54 | 78 |
| 4 | 0.63 | 58 | 75 |
| 5 | 1.03 | 59 | 76 |
| 6 | 2.89 | 62 | 77 |

Note
*1 the amount of cymene hydroperoxide accumulated per the unit volume of the reaction vessel for the unit time
*2 the ratio (%) of the mole of formed cymene hydroperoxide to the mole of consumed starting cymene

COMPARATIVE EXAMPLE 1

By using the same continuous oxidation vessel as used in Examples 1 to 6, continuous oxidation of a mixture of m- and p-cymenes was carried out under conditions of a reaction temperature of 120° C., a reaction pressure of 5 $Kg/cm^2$-G, an agitation rate of 750 rpm, an aqueous phase pH of 8.0 and an oily phase/aqueous phase volume ratio of 9/1 without using the copper catalyst. The CyHP concentration in the liquid reaction mixture was maintained at 14.7% by weight by adjusting the residence time of starting cymene. The CyHP accumulation rate and oxidation efficiency were 27 g/l.hr and 69 mol %, respectively.

COMPARATIVE EXAMPLE 2

By using the same continuous oxidation vessel as used in Examples 1 to 6, continuous oxidation of a mixture of m- and p-cymenes was carried out under conditions of a reaction temperature of 120° C., a reaction pressure of 5 $Kg/cm^2$-G, an agitation rate of 750 rpm, an aqueous phase pH of 8.0 and an oily phase/aqueous phase volume ratio of 9/1 by adding a copper sulfate catalyst at a copper atom concentration of 12 ppm based on the entire liquid phase, while maintaining the CyHP concentration in the liquid reaction mixture at 14.5% by weight. The CyHP accumulation rate and oxidation efficiency were 32 g/l.hr and 42 mol %, respectively.

EXAMPLES 7 to 10

By using the same continuous oxidation vessel as used in Examples 1 to 6, continuous oxidation of a mixture of m- and p-cymenes was carried out under conditions of a reaction temperature of 120° C., a reaction pressure of 5 Kg/cm²-G and an agitation rate of 750 rpm in the presence of a copper sulfate catalyst at a copper atom concentration of 0.15 ppm based on the liquid phase, while maintaining the CyHP concentration in the liquid reaction mixture at 14 to 15% by weight by controlling the residence time of starting cymene. The pH value of the aqueous phase was set at 7.7, 7.8, 8.1 or 8.5 by changing the feed rate of the 4% aqueous solution of sodium carbonate. The obtained results are shown in Table 2.

TABLE 2

| Example No. | pH Value of Aqueous Phase | CyHP Accumulation Rate (g/l . hr) | Oxidation Efficiency (mol %) |
|---|---|---|---|
| 7 | 7.7 | 51 | 78 |
| 8 | 7.8 | 53 | 80 |
| 9 | 8.1 | 52 | 77 |
| 10 | 8.5 | 51 | 78 |

COMPARATIVE EXAMPLES 3 and 4

By using the same continuous oxidation vessel as used in Examples 1 to 6, continuous oxidation of a mixture of m- and p-cymenes was carried out under the same conditions as in Examples 7 to 10 except that the pH value of the aqueous phase was changed to 7.3 or 10.6. When the pH value of the aqueous phase was 7.3, the CyHP accumulation rate and oxidation efficiency were 36 g/l.hr and 70 mol %, respectively, and when the pH value of the aqueous phase was 10.6, the CyHP accumulation rate and oxidation efficiency were 29 g/l.hr and 69 mol %, respectively.

EXAMPLES 11 to 13

By using the same continuous oxidation vessel as used in Examples 1 to 6, continuous oxidation of a mixture of m- and p-cymenes was carried out under conditions of a reaction temperature of 120° C., a reaction pressure of 5 Kg/cm²-G, an agitation rate of 750 rpm and an aqueous phase pH value of 7.9 in the presence of a copper sulfate catalyst at a copper atom concentration of 0.21 ppm based on the liquid phase. The volume ratio of the aqueous phase to the oily phase was adjusted to 8/92, 19/81 or 31/69. The obtained results are shown in Table 3.

TABLE 3

| Example No. | Aqueous Phase/ Oily Phase Volume Ratio | CyHP Accumulation Rate (g/l . hr) | Oxidation Efficiency (mol %) |
|---|---|---|---|
| 11 | 8/92 | 52 | 79 |
| 12 | 19/81 | 53 | 80 |
| 13 | 31/69 | 52 | 78 |

EXAMPLES 14 to 17

By using the same continuous oxidation vessel as used in Examples 1 to 6, continuous oxidation of a mixture of m- and p-cymenes was carried out under the same conditions as in Examples 2 except that copper (II) nitrate, cupric (II) chloride, copper (II) acetate or copper (II) stearate was used as the catalyst instead of copper (II) sulfate. The obtained results are shown in Table 4.

TABLE 4

| Example No. | Catalyst | CyHP Accumulation Rate (g/l . hr) | Oxidation Efficiency (mol %) |
|---|---|---|---|
| 14 | copper (II) nitrate | 52 | 79 |
| 15 | copper (II) chloride | 53 | 78 |
| 16 | copper (II) acetate | 54 | 80 |
| 17 | copper (II) stearate | 52 | 79 |

What we claim is:

1. A process for the preparation of aromatic hydroperoxides which comprises reacting an aromatic compound represented by the following formula:

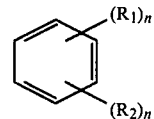

wherein $R_1$ stands for a secondary alkyl group having 3 to 4 carbon atoms, $R_2$ stands for a primary alkyl group having up to 4 carbon atoms, and n and m are numbers of 1 or 2 with the proviso that the sum of n and m does not exceed 3, with a molecular oxygen-containing gas in two liquid phases which comprise an oily phase containing the aromatic compound and a basic aqueous phase under agitation at a temperature of from room temperature to 200° C. under a pressure of 1 to 50 Kg/cm² gauge, wherein a copper compound catalyst composed of an inorganic salt or organic acid salt of copper which is soluble in the basic aqueous phase is present in the liquid phases at a concentration of 0.005 to 10 ppm as the copper atom, the pH value of the basic aqueous phase is maintained at 7.6 to 10, and the volume ratio of the basic aqueous phase to the oily phase is in the range of from 0.001 to 1.

2. A process for the preparation of aromatic hydroperoxides according to claim 1, wherein the concentration of the copper compound catalyst in the liquid phases is 0.02 to 5 ppm as the copper atom.

3. A process for the preparation of aromatic hydroperoxides according to claim 1, wherein the pH value of the basic aqueous phase was maintained at 7.7 to 8.7.

4. A process for the preparation of aromatic hydroperoxides according to claim 1, wherein the aromatic compound is cymene, dimethylcumene or diisopropyltoluene.

5. A process for the perparation of aromatic hydroperoxides according to claim 1, wherein the liquid phase catalytic oxidation is carried out at a temperature of 60° to 150° C.

6. A process for the preparation of aromatic hydroperoxide according to claim 2 wherein the concentration of the copper compound catalyst in the liquid phase is 0.05 to 3 ppm as the copper atom.

7. A process for the production of aromatic hydroperoxides according to claim 1 wherein the reaction is conducted in the presence of a solvent which is capable of dissolving therein the aromatic compound, insoluble in the basic aqueous solution phase and inactive to the oxidation, the weight ratio of the solvent to the aromatic compound being in the range of from 0.01 to 100.

8. A process for the production of aromatic hydroperoxides according to claim 7 wherein the solvent is selected from the group consisting of benzene, clorbenzene, dichlorobenzene, and trifluoromethylbenzene.

* * * * *

UNITED STATES PATENT AND TRADEMARK OFFICE
CERTIFICATE OF CORRECTION

PATENT NO. : 4,288,637
DATED : September 8, 1981
INVENTOR(S) : Matsunaga, et al.

It is certified that error appears in the above—identified patent and that said Letters Patent is hereby corrected as shown below:

Claim 8, lines 4-5, "clorbenzene" should read -- chlorbenzene --

Signed and Sealed this

Tenth Day of November 1981

[SEAL]

Attest:

Attesting Officer

GERALD J. MOSSINGHOFF

Commissioner of Patents and Trademarks